(12) United States Patent
Li et al.

(10) Patent No.: US 10,888,416 B2
(45) Date of Patent: Jan. 12, 2021

(54) THREE DIMENSIONAL TISSUE PRINTING DEVICE, THREE DIMENSIONAL TISSUE PRINTING METHOD AND ARTIFICIAL SKIN

(71) Applicant: INDUSTRIAL TECHNOLOGY RESEARCH INSTITUTE, Hsin-chu (TW)

(72) Inventors: Chang-Chou Li, Tainan (TW); Li-Wen Lai, Taichung (TW); Yang-Cheng Lin, Chiayi (TW); Chin-Lung Liu, Kaohsiung (TW); Chih-Yu Ke, Pingtung (TW); Teng-Yen Wang, Yunlin County (TW)

(73) Assignee: INDUSTRIAL TECHNOLOGY RESEARCH INSTITUTE, Hsin-Chu (TW)

( * ) Notice: Subject to any disclaimer, the term of this patent is extended or adjusted under 35 U.S.C. 154(b) by 965 days.

(21) Appl. No.: 14/971,211

(22) Filed: Dec. 16, 2015

(65) Prior Publication Data
US 2017/0136700 A1     May 18, 2017

(30) Foreign Application Priority Data

Nov. 13, 2015   (TW) .............................. 104137567 A

(51) Int. Cl.
| | | |
|---|---|---|
| *B29C 67/00* | (2017.01) | |
| *A61F 2/10* | (2006.01) | |
| *B29C 64/112* | (2017.01) | |
| *B29C 64/245* | (2017.01) | |
| *B29C 64/295* | (2017.01) | |
| *B29C 64/314* | (2017.01) | |
| *B29C 64/364* | (2017.01) | |
| *B29C 64/106* | (2017.01) | |
| *A61L 27/18* | (2006.01) | |
| *A61L 27/24* | (2006.01) | |
| *A61L 27/38* | (2006.01) | |
| *A61L 27/60* | (2006.01) | |
| *C12N 5/071* | (2010.01) | |
| *B29C 64/209* | (2017.01) | |
| *B33Y 10/00* | (2015.01) | |
| *B33Y 30/00* | (2015.01) | |
| *B33Y 80/00* | (2015.01) | |
| *B29K 105/00* | (2006.01) | |
| *B29L 31/00* | (2006.01) | |

(52) U.S. Cl.
CPC .............. *A61F 2/105* (2013.01); *A61L 27/18* (2013.01); *A61L 27/24* (2013.01); *A61L 27/3839* (2013.01); *A61L 27/60* (2013.01); *B29C 64/106* (2017.08); *B29C 64/112* (2017.08); *B29C 64/245* (2017.08); *B29C 64/295* (2017.08); *B29C 64/314* (2017.08); *B29C 64/364* (2017.08); *C12N 5/0698* (2013.01); *A61L 2430/34* (2013.01); *B29C 64/209* (2017.08); *B29K 2105/0058* (2013.01); *B29K 2105/251* (2013.01); *B29K 2995/006* (2013.01); *B29K 2995/0012* (2013.01); *B29L 2031/7532* (2013.01); *B33Y 10/00* (2014.12); *B33Y 30/00* (2014.12); *B33Y 80/00* (2014.12)

(58) Field of Classification Search
CPC ..... A61F 2/105; B29C 64/245; B29C 64/295; B29C 64/314; B29C 64/364; B29C 64/106; B29C 64/112; B29C 64/209; A61L 27/18; A61L 27/24; A61L 27/3839; A61L 27/60; A61L 2430/34; A61L 27/3804; C12N 5/0698; B33Y 10/00; B33Y 30/00; B33Y 80/00; B29K 2105/0058; B29K 2105/251; B29K 2995/0012; B29K 2995/006; B29L 2031/7532; C08L 67/04
See application file for complete search history.

(56) References Cited

U.S. PATENT DOCUMENTS

| | | |
|---|---|---|
| 4,759,764 A | 7/1988 | Fawcett et al. |
| 6,315,469 B1 | 11/2001 | Alvarez et al. |
| 7,625,198 B2 | 12/2009 | Lipson et al. |
| 8,241,905 B2 | 8/2012 | Forgacs et al. |
| 8,931,880 B2 | 1/2015 | Murphy et al. |
| 9,018,008 B2 | 4/2015 | Cho et al. |
| 2008/0070304 A1 | 3/2008 | Forgacs et al. |
| 2010/0038830 A1 | 2/2010 | Lahann et al. |

(Continued)

FOREIGN PATENT DOCUMENTS

| | | |
|---|---|---|
| CN | 103083719 A | 5/2013 |
| CN | 103341989 A | 10/2013 |

(Continued)

OTHER PUBLICATIONS

Sean V Murphy et al., 3D bioprinting of tissues and organs, Nature Biotechnology, 2014, 32, 773-785.
Billiet, T. et al., A review of trends and limitations in hydrogelrapid prototyping for tissue engineering, Biomaterials, 2012, 33, 6020-6041.
Shinjiro Umezu et al., Characteristics on micro-biofabrication by patterning with electrostatically injected droplet, CIRP Annals—Manufacturing Technology, 2014, 63, Issue 1, 221-224.

(Continued)

*Primary Examiner* — Titilayo Moloye
(74) *Attorney, Agent, or Firm* — Locke Lord LLP; Tim Tingkang Xia, Esq.

(57) ABSTRACT

A three dimensional tissue printing method is disclosed. The three dimensional tissue printing method includes the following steps: performing large support stand printing to form a first printing body; performing small support stand printing to form second printing body on the first printing body and forming a tissue structure by crossly connecting in between the first printing body and the second printing body. Besides, a three dimensional tissue printing device and artificial skin are also presented.

15 Claims, 15 Drawing Sheets

(56) References Cited

U.S. PATENT DOCUMENTS

| | | |
|---|---|---|
| 2012/0089238 A1 | 4/2012 | Kang et al. |
| 2013/0216724 A1 | 8/2013 | Lee et al. |
| 2015/0037445 A1* | 2/2015 | Murphy .............. B29C 64/386 |
| | | 425/131.1 |
| 2015/0054201 A1 | 2/2015 | Kim et al. |
| 2015/0119994 A1 | 4/2015 | Kang et al. |
| 2015/0230912 A1 | 8/2015 | Lee et al. |

FOREIGN PATENT DOCUMENTS

| | | |
|---|---|---|
| CN | 103407292 A | 11/2013 |
| CN | 103587119 A | 2/2014 |
| CN | 103612391 A | 3/2014 |
| CN | 104383604 A | 3/2015 |
| CN | 104441654 A | 3/2015 |
| CN | 104667344 A | 6/2015 |
| CN | 104690961 A | 6/2015 |
| CN | 104742369 A | 7/2015 |
| CN | 104985822 A | 10/2015 |
| CN | 204734579 U | 11/2015 |
| DE | 10018987 A1 | 10/2001 |
| TW | 1459978 B | 11/2014 |
| TW | 201522090 A | 6/2015 |
| WO | 2015066705 A1 | 5/2015 |

OTHER PUBLICATIONS

Chen Guang et al., Introduction to New Materials, Material Science and Engineering for General Higher Education 125, National Defense Industry Press, Beijing, 2013.

Gu, Ji-Xing et al., Collagen-based Biomaterials in Clinical Medicine, Series of Natural Degradable Biomedical Materials, 2003.

* cited by examiner

THREE DIMENSIONAL TISSUE PRINTING DEVICE, THREE DIMENSIONAL TISSUE PRINTING METHOD AND ARTIFICIAL SKIN

CROSS REFERENCE TO RELATED APPLICATION

This application also claims priority to Taiwan Patent Application No. 104137567 filed in the Taiwan Patent Office on Nov. 13, 2015, the entire content of which is incorporated herein by reference.

TECHNICAL FIELD

The disclosure relates to a printing device, printing method and artificial skin, and more particularly, to a three dimensional tissue printing device, three dimensional tissue printing method and artificial skin.

BACKGROUND

Following the progress of computer-aided manufacturing (CAM), the manufacturers develop a technology of three dimensional printing capable of rapidly manufacturing the original conceptual design.

Additive manufacturing is a rapid prototyping technology and its manufacturing process is to establish a three dimensional model through the computer-aided design, and then to have the model segment horizontally into cross-sections by tiny intervals, afterward, making use of the manufacturing facilities to have the liquid, powder, strip-shaped or flake-shaped material to be printed layer by layer according to the shape of the cross-section, cure and join, and then pack up to become entity. Conventional cutting working employs "subtraction" to have a lump of material remove the unwanted parts while the additive manufacturing employs "addition" to have the needed parts deposited into three dimensional structure by the way similar to the printing, thereby, is called three dimensional printing technology.

The above-mentioned three dimensional printing technology can not only overcome the difficulty that the machine tool is unable to accomplish complicated geometric shape but is also capable of rapidly forming the prototype without being limited to their shapes, thereby, is favored in the market. Through years of progressing, from mainly manufacturing the prototype of polymer material to the development of industrial goods and tool, the biomedical material, and the required biomedical products such as medical aided appliance, scaffold used for tissue working frame etc. are also able to be working and fabricated. Among them, the successful medical programs of tissue regeneration and reconstruction technology are the most challenging directions of development, and the maximum efficacy and benefit for human being.

Although the period of the technological development of tissue engineering has been over twenty one years, a big break through has not been able to accomplish. The main reason is that the existing technology is unable to manufacture and produce complicated tissue structure that possesses required functions. Recently, the three dimensional tissue printing technology makes the development of tissue engineering technology a new beam of hope. Conceptually, the three dimensional tissue printing technology can appears the correct positions of the cells in the tissue, cell interstitial and active molecules at each point in the three dimensional space, and can fabricate the products of different appearances, different cells or active molecular density. For the idea of tissue printing, although the overall concept have been formed, as far as the existing machine of printing tissue as concerned, the printed out product is merely a macromolecule tissue prosthesis possessing the tissue appearance. How to provide a tissue structure of appropriate growth environment for the cell still needs breakthroughs for the bottlenecks.

SUMMARY

The disclosure provides a three dimensional tissue printing device capable of providing the integrity and mechanical strength of the three dimensional tissue structure, also capable of having the precision of "printing the micro structure" improve up to 20~200 micron, and further capable of maintaining the cell function after printing to avoid gene mutation and functional variation of the cell.

The disclosure provides a three dimensional tissue printing method capable of establishing a three dimensional tissue structure for providing sufficient mechanical strength for the tissue and having the precision of "printing the micro structure" improve up to 20~200 micron, and further establish a three dimensional tissue structure suitable for the conditions of cell growth.

The disclosure provides an artificial skin formed by printing through the use of the above-mentioned three dimensional tissue printing device and method. These facilities and methods is capable of performing customized printing. What is more, as the artificial skin contains growth factors, it can promotes the growth of the skin.

An embodiment of the disclosure provides a three dimensional tissue printing device which includes a three dimensional moving platform, an instillation unit, and a carrier unit. The instillation unit, being connected to the three dimensional moving platform, further comprising a large support stand printing device and a small support stand printing device. Among them, the large support stand printing device being used for filling a temperature-reaction type material further comprising a temperature-controlled modulation module, while the small support stand printing device is used for filling a material. The carrier unit, being connected to the three dimensional moving platform and positioned opposite to the instillation unit further comprising a heating element, wherein, the temperature-controlled modulation module is used for cooling the temperature-reaction type material contained in the large support stand printing device; the three dimensional moving platform moves the large support stand printing device which has the temperature-reaction type material, after being cooled down, squeezes out to the carrier unit; the heating element, heats the temperature-reaction type material, after being cooled, to form a first printing body; the small support stand printing device, after being exerted electric voltage, generates voltage difference with the carrier unit making the material contained in the small support stand printing device form a micro jet stream; the three dimensional moving platform moves the small support stand printing device to make the micro jet stream print on the first printing body to form a second printing body; and a tissue structure is formed by crossly connecting between the first printing body and the second printing body.

An embodiment of the disclosure provides a three dimensional tissue printing method which includes the following steps: performing a large support stand printing to form a first printing body, and performing a small support stand printing to form a second printing body on the first printing body, wherein, a tissue structure is formed by crossly connecting in between the first printing body and the second printing body.

An embodiment of the disclosure provides an artificial skin which includes a first printing body, a second printing body, and a plurality of human-body fiber mother cells. The first printing body is constituted by a temperature-reaction type material, and through the process of cooling the temperature-reaction type material and curing, the material form a micro jet stream that prints on the first printing body to form a second printing body, and a tissue structure is formed by crossly connecting in between the first printing body and the second printing body, and the plurality of human-body fiber mother cells are positioned at the tissue structure formed by crossly connecting in between the first printing body and the second printing body.

Based on the above statements, in the three dimensional tissue printing device, the three dimensional tissue printing method, and the artificial skin of the disclosure, the first printing body is constituted by the temperature-reaction type material. The temperature-reaction type material appears flow-state through the cooling process. The flow-state temperature-reaction type material is performed moving-and-printing on the bearing plate and formed the first printing body through heating and curing process for providing a main support stand that possesses mechanical strength. Subsequently, through exerting electric voltage to make the material form micro jet stream, the micro jet stream will be printed on the first printing body to form a second printing body which provides cell connection, and since the line width of small support stand printing device is relatively smaller, making them capable of being established between the first printing bodies and is formed a tissue structure in between with the second printing body for providing sufficient mechanical strength.

BRIEF DESCRIPTION OF THE DRAWINGS

The accomplishment of this and other objects of the disclosure will become apparent from the following description and its accompanying drawings of which.

DETAILED DESCRIPTION OF THE PREFERRED EMBODIMENT

The following descriptions are embodiments of the disclosure employing some particular concrete examples. Those people skilled in the art are capable of easily realizing the advantages and efficacies of the disclosure through the content disclosed by the patent specification of the disclosure.

Figure 1:
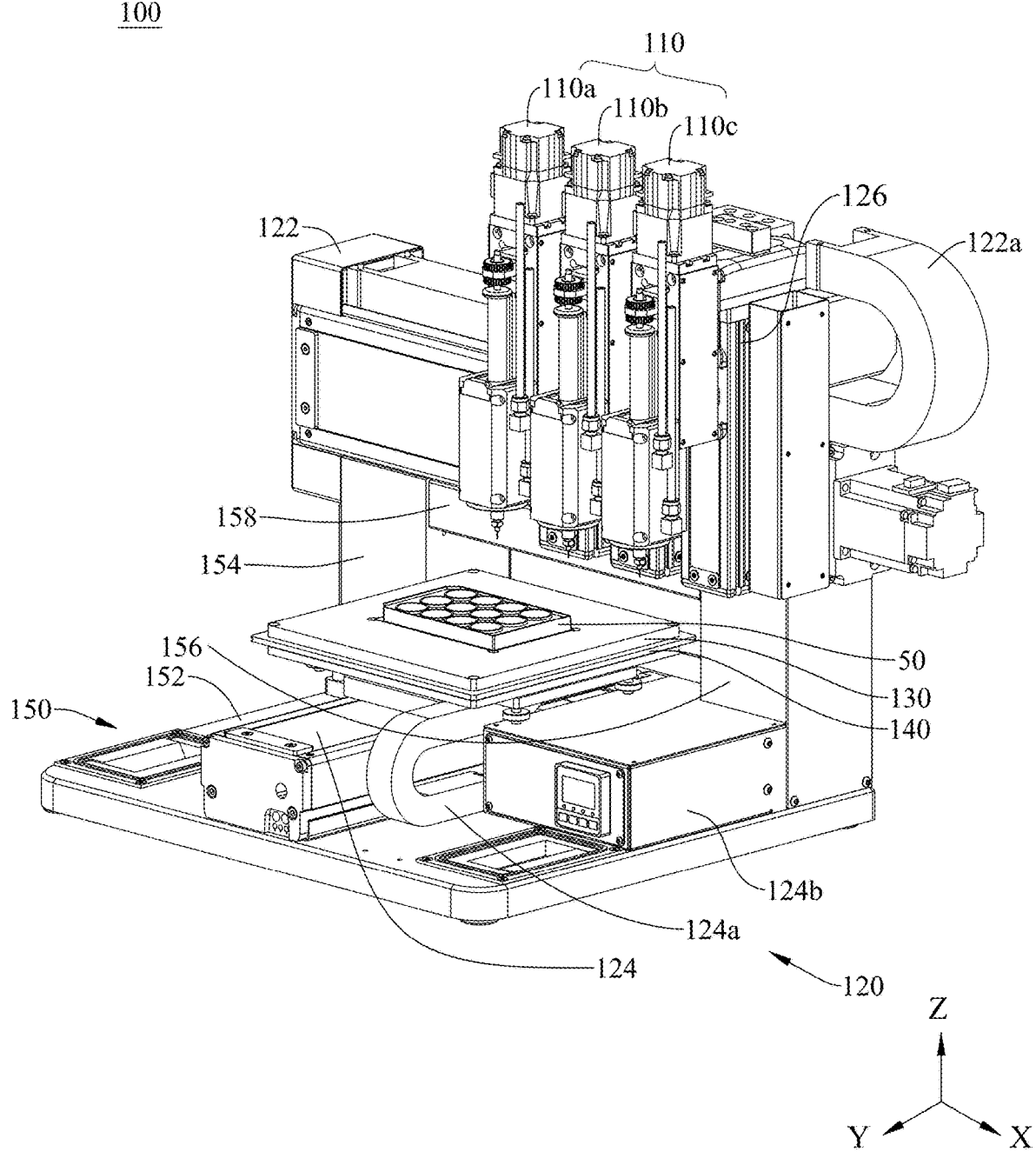
FIG. 1 is a schematic drawing of the three dimensional tissue printing device of the disclosure.
Figure 2:
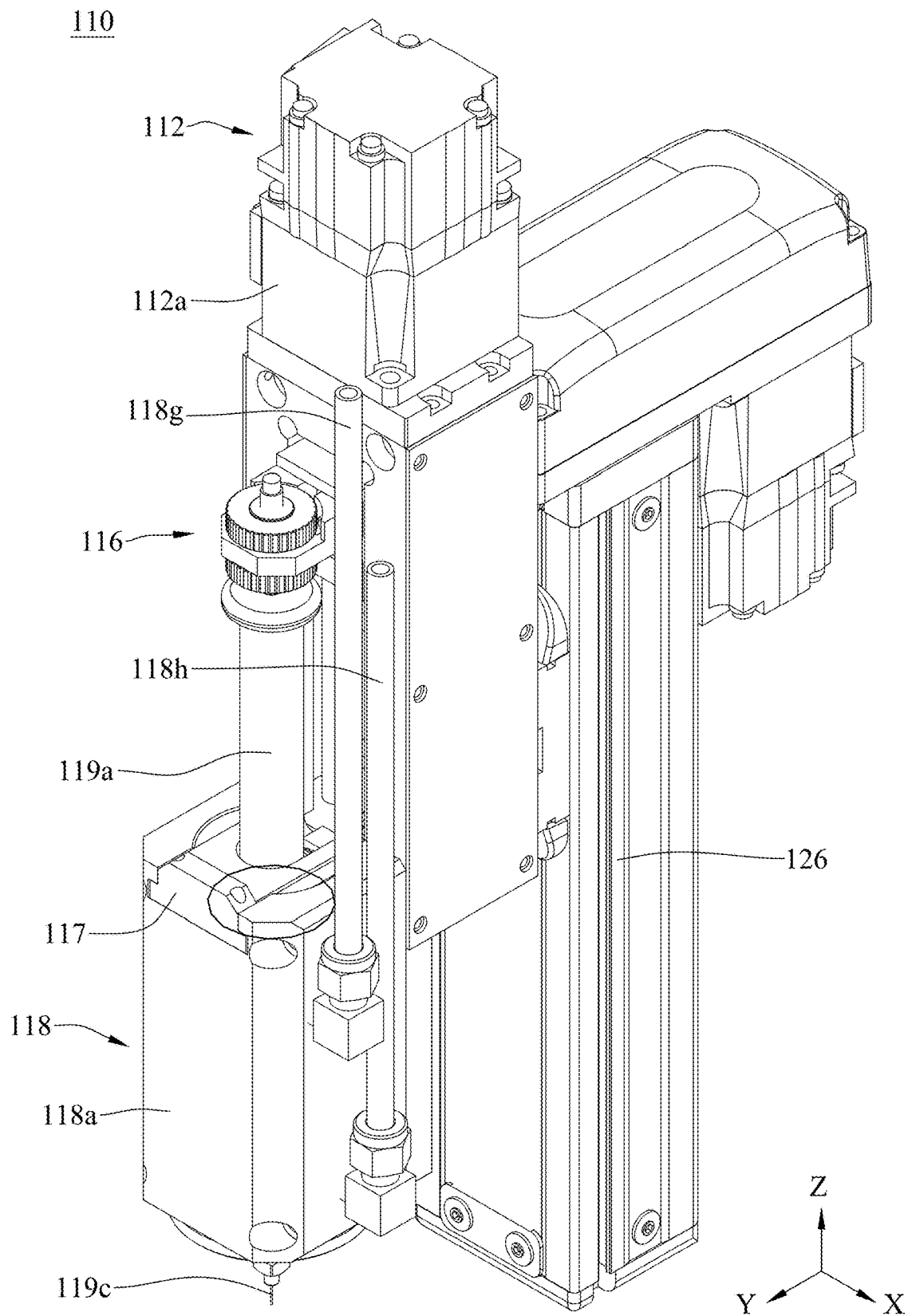
FIG. 2 is a partial schematic drawing of the infusion unit and the Z-axis driving element of the disclosure.

FIG. 1 is a schematic drawing of the three dimensional tissue printing device of the disclosure while FIG. 2 is a partial schematic drawing of the infusion unit and the Z-axis driving element of the disclosure. Firstly, as shown in FIG. 1, in the present embodiment, the three dimensional tissue printing device (100) includes a instillation unit (110), a three dimensional moving platform (120) and a carrier unit (130) wherein both the instillation unit (110) and the carrier unit (130) are connected to the three dimensional moving platform (120) and the carrier unit (130) and the instillation unit (110) are mutually opposite.

The three dimensional moving platform (120) includes a base seat (150), an X-axis driving element (122), a Y-axis driving element and a Z-axis driving element (126) wherein the X-axis driving element (122), the Y-axis driving element and the Z-axis driving element (126) are furnished on the base seat (150) respectively.

To depict in detail, the base seat (150) includes a bottom part (152), a left support stand (154), a right support stand (156) and a base seat back plate (158) wherein the left support stand (154) and the right support stand (156) are furnished on the bottom part (152) while the base seat back plate (158) is securely clipped by the left support stand (154) and the right support stand (156).

The Y-axis driving element (124) being positioned on the bottom part (152) includes a Y-axis cable protecting tube (124a) and a Y-axis trunking box (124b) wherein the Y-axis cable protecting tube (124a) is positioned between the Y-axis driving element (124) and the Y-axis trunking box (124b).

The carrier unit (130), being positioned on the Y-axis driving element (124) which is capable of driving the carrier unit (130) to move along the Y-axis direction, includes a heating element (140) and a cultivation dish (50).

The X-axis driving element (122) and the Z-axis driving element (126) are installed at the left support stand (154) and the right support stand (156) respectively where the X-axis driving element (122) includes an X-axis cable protecting tube (122a).

It should be noted that the Z-axis driving element (126), whose inner structure can be seen in FIG. 2, shown in FIG. 1 is covered and shielded by a sheet metal part. The instillation unit (110), being furnished in the Z-axis driving element (126) that is capable of driving the instillation unit (110) to move in Z-axis direction, includes a large support stand printing device (110a), a small support stand printing device (110b) and a cell printing device (110c). It should be also noted that the small support stand printing device (110b) shown in FIG. 1 is arranged between the large support stand printing device (110a) and cell printing device (110c), but this is not limited in the present embodiment, it all depends on the real situation that the arrangement order of the large support stand printing device (110a), the small support stand printing device (110b) and the cell printing device (110c) can be adjusted.

Figure 3:
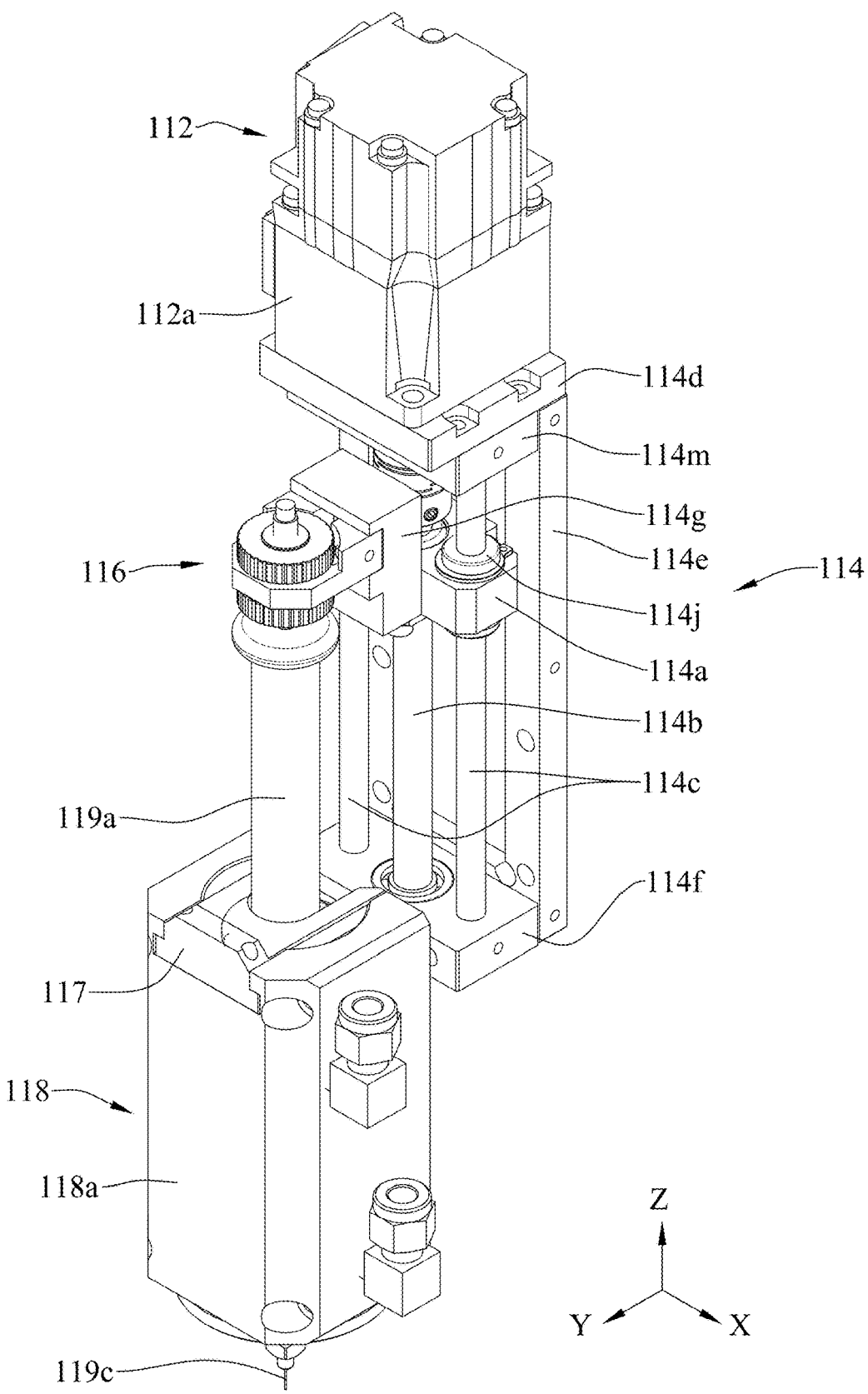
FIG. 3 is a schematic drawing of the infusion unit of the disclosure.
Figure 4:
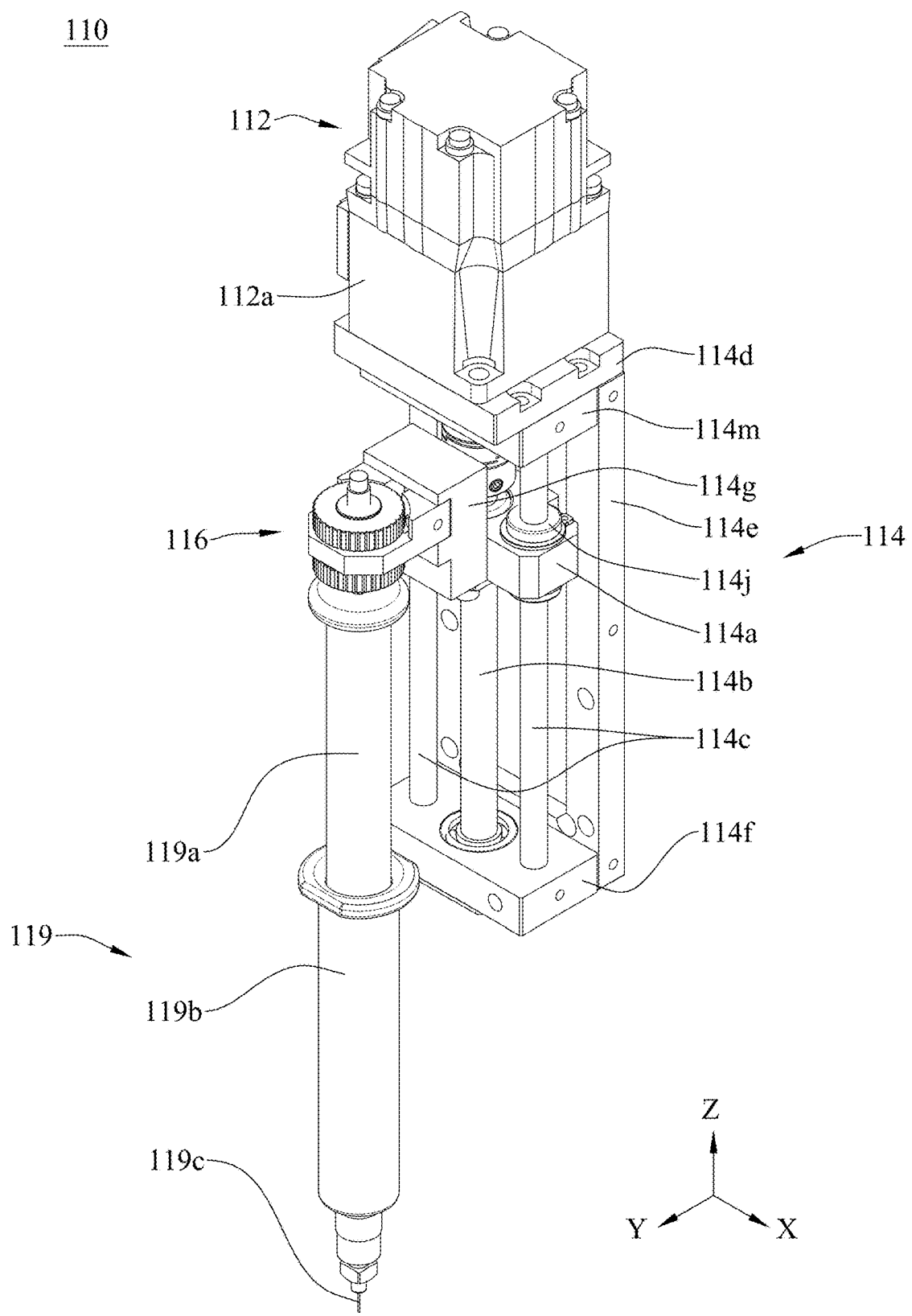
FIG. 4 is a schematic drawing of the partial structural members of the infusion unit in FIG. 3 of the disclosure.
Figure 5:
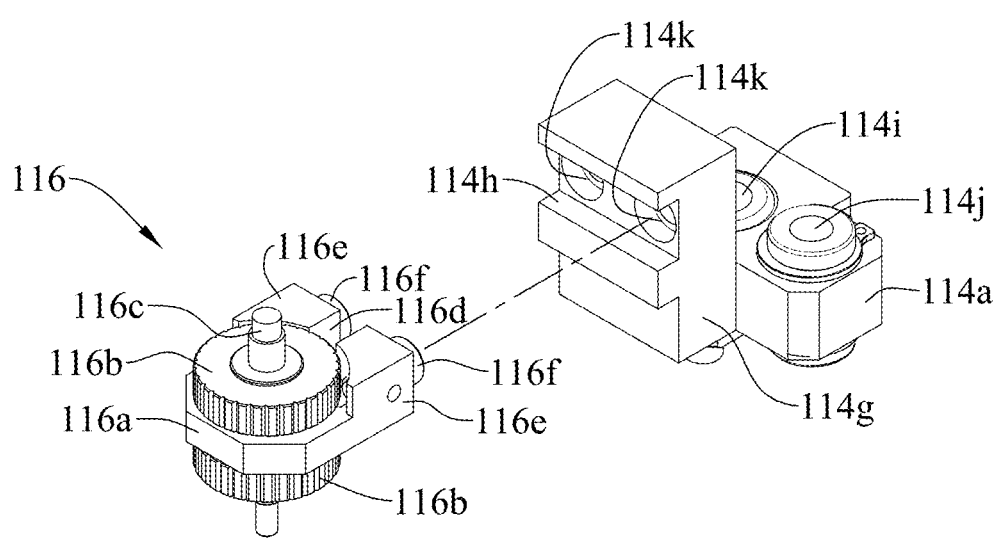
FIG. 5 is a schematic drawing of the partial structural members of the quick-released platen assembly in FIG. 3 of the disclosure.
Figure 6:
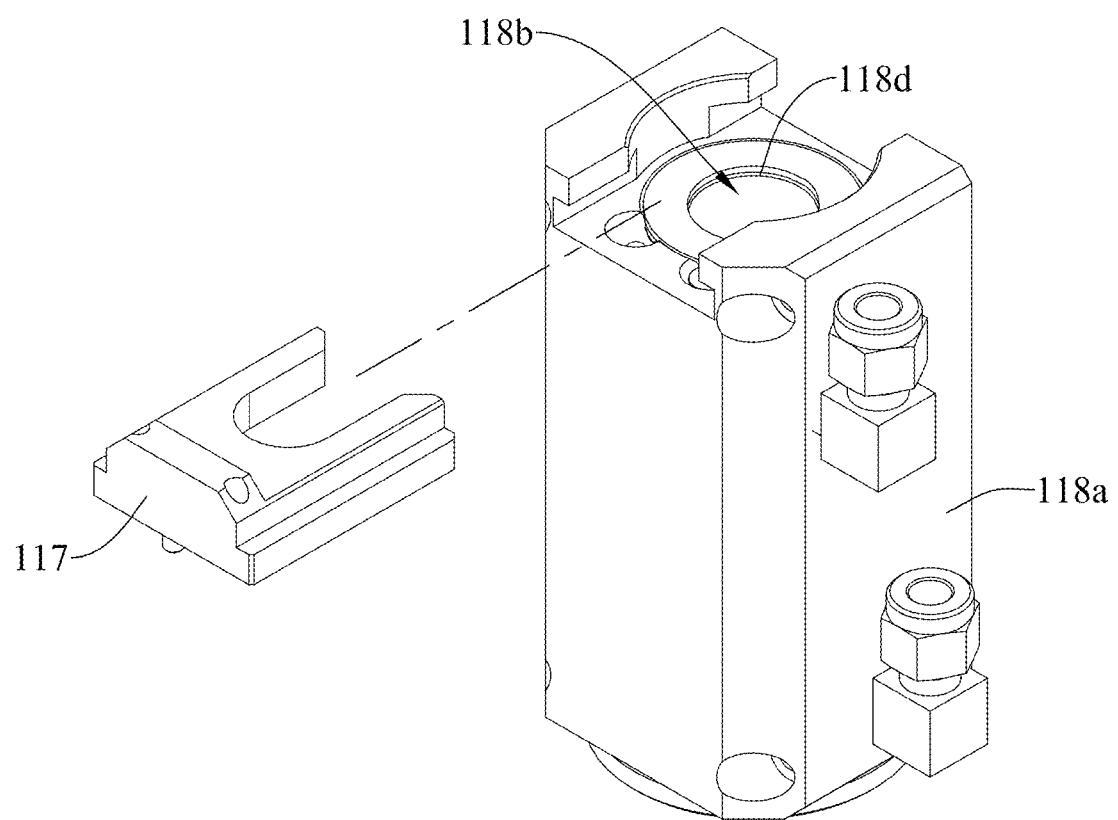
FIG. 6 is a schematic drawing of the temperature-controlled modulation module and syringe platen in FIG. 3 of the disclosure.

FIG. 3 is a schematic drawing of the infusion unit of the disclosure; FIG. 4 is a schematic drawing of the partial structural members of the infusion unit in FIG. 3 of the disclosure; FIG. 5 is a schematic drawing of the partial structural members of the quick-released platen assembly in FIG. 3 of the disclosure; while FIG. 6 is a schematic drawing of the temperature-controlled modulation module and syringe platen in FIG. 3 of the disclosure.

As shown in FIG. 2 through FIG. 6, the instillation unit (110) includes a driving motor (112), a driving-sliding platform (114), a rapidly releasing platen assembly (116), a syringe platen (117), a temperature-controlled modulation module (118) and an injection device (119).

The driving motor (112) being connected to the driving-sliding platform (114) includes a reducer (112a). The rapidly releasing platen assembly (116) is furnished on the driving-sliding platform (114).

The injection device (119) includes an injection push rod (119a), an injection barrel (119b) and a pinhead (119c) wherein the injection barrel (119b) is furnished through the temperature-controlled modulation module (118), and the syringe platen (117) is inserted into the temperature-controlled modulation module (118) for withholding the injection barrel (119b), and the pinhead (119c) is positioned at an end of the injection barrel (119b) while an end of the injection push rod (119a) is movably inserted in the injection barrel (119b) with another end of the injection push rod (119a) connected to the driving-sliding platform (114) through the rapidly releasing platen assembly (116).

As shown in FIG. 3 through FIG. 5, in the present embodiment, the driving-sliding platform (114) includes a top plate (114d), a side plate (114e), a bottom plate (114f), a bearing plate (114m), two guided rods (114c), a ball screw (114b), a securing member (114a), a connecting member (114g), two linear bushings (114j), a ball screw nut (114i), an indentation (114h) and two magnetic elements (114k).

As shown in FIG. 3 and FIG. 4, the top end and the bottom end of the side plate (114e) are perpendicularly connected to the top plate (114d) and the bottom plate (114f) respectively to form a containing space. The reducer (112a) of the driving motor (112) is positioned on the top plate (114d) while the bearing plate (114m) is positioned beneath the top plate (114d). The securing member (114a), the ball screw (114b), the two guided rods (114c), the two linear bushings (114j) and a ball screw nut (114i) (see FIG. 5) are all positioned in this containing space.

To state in detail, the two guided rods (114c) are positioned on both sides of the ball screw (114b), the two linear bushings (114j) are positioned on both sides of the ball screw (114i). The two guided rods (114c) are sleeved into the two linear bushings (114j) while the ball screw (114b) is sleeved into the ball screw nut (114i). The connecting member (114g) is connected to the securing member (114a). The indentation (114h) is formed at the connecting member (114g) while the two first magnetic elements (114k) are positioned within the indentation (114h).

The rapidly releasing platen assembly (116) includes a platen (116a), two embossment added nuts (116b), a push rod screw (116c), a trench (116d), two salient parts (116e) and the second magnetic element (116f).

The two embossed nuts (116b) are furnished on both sides of the platen (116a) respectively. The push rod screw (116c) being penetrated through the two embossed nuts (116b) and platen (116a) has an end connected to injection push rod (119a).

In the present embodiment, the platen (116a) being structurally a horseshoe-shape itself has an end thereof possess the two salient parts (116e). The trench (116d) is formed between the two salient parts (116e) of the platen (116a). The two second magnetic elements (116f) being furnished on the platen (116) are positioned on both sides of the trench (116d) respectively. Based on this, the two first magnetic elements (114k) and the two second magnetic elements (116f) are mutually attracted making the platen (116a) connect to the connecting member (114g).

Under this disposition, the driving motor (112) drives the ball screw (114b) making the ball screw (114b) and the ball screw nut (114i) perform relative rotation. Since both ends of the ball screw (114b) are pivotally supported, it makes the ball screw nut (114i) be driven by the ball screw (114b) to rotate and the securing member (114a) is performed up-and-down linear movement in Z-direction on the two guided rods (114c) to push the injection push rod to move along within the injection barrel. In other embodiments not shown in the Figures, a guidance mode of linear sliding rail and slider can be employed or a pneumatic pushing mode can also be employed to push the injection push rod to be moved within the injection barrel, but the present embodiment is not limited to these.

Figure 7:
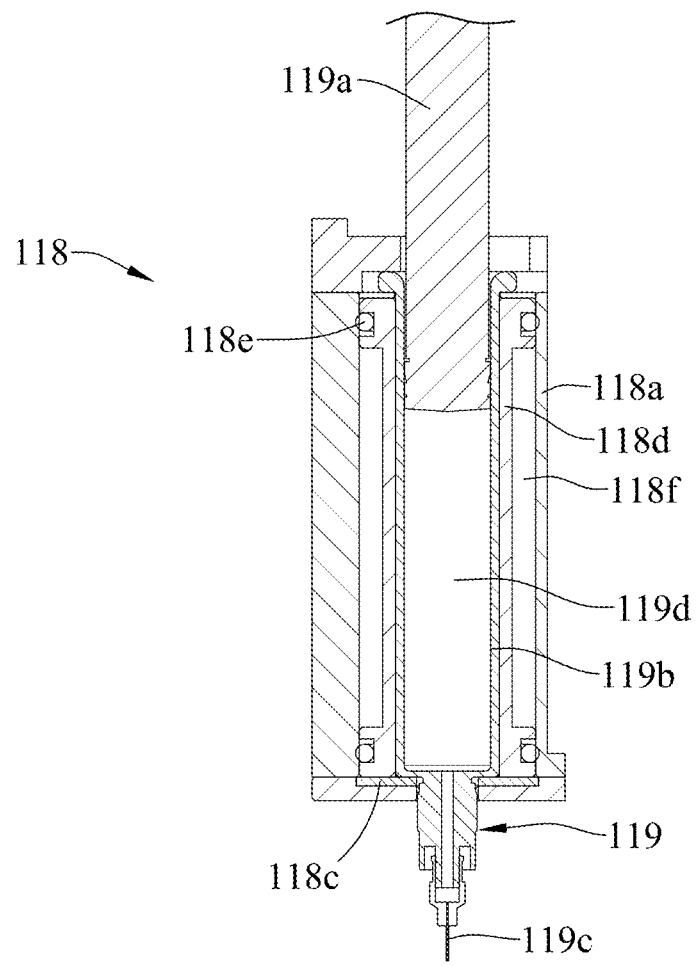
FIG. 7 is a schematic cross-sectional drawing of the temperature-controlled modulation module and injection device in FIG. 3 of the disclosure.

FIG. 7 is a schematic cross-sectional drawing of the temperature-controlled modulation module and injection device in FIG. 3 of the disclosure, Please refer to FIG. 2, FIG. 3, FIG. 6 and FIG. 7.

In the present embodiment, the temperature-controlled modulation module (118) includes cooling water ring jacket (118a), a containing part (118b), cool-guidance washer (118c), a cooling inner ring (118d), an O-ring (118e), a heat-exchange area (118f), a first temperature modulation pipeline (118g), a second temperature modulation pipeline (118f).

As shown in FIG. 2, the first temperature modulation pipeline (118g) and the second temperature modulation pipeline (118f) are communicated to the inner part of the cooling water ring jacket (118a) such that the first temperature modulation pipeline (118g) and the second temperature modulation pipeline (118f) are able to outwardly connected to a water source supply device (not shown in the Figure). In the present embodiment, the water source supply device, for instance, can be a chiller which is capable of providing ice water by the way of performing heat exchanging with refrigerant.

Referring again to FIG. 3, FIG. 6 and FIG. 7, the cooling inner ring being furnished in the cooling water ring jacket (118a) forms the heat-exchange area (118f) there between, while the first temperature modulation pipeline (118g) and the second temperature modulation pipeline (118f) are communicated within the heat-exchange area (118f). The O-ring (118e) is positioned between the cooling water ring jacket (118a) and the cooling inner ring (118d) for preventing the liquid from leaking from the junction between cooling water ring jacket (118a) and cooling inner ring (118d). The cool-guidance washer (118c) being positioned between the front end of the injection barrel (119b) and the cooling water ring jacket (118a) have the heat at low-temperature therein transfer by conduction to the pinhead (119c) to maintain the pinhead (119c) at low temperature as within the injection barrel (119b) to enhance the cool-maintaining effect of the temperature-reaction mode of material.

The injection barrel (119b) being positioned within the containing part (118b) formed by the cooling inner ring (118d) possesses a material feeding area (119d). In the present embodiment, the material feeding area (119d) is capable of filling the corresponding material depending on the what kind of printing device it is. In an embodiment, the collagen of the temperature-reaction type material is filled in the material feeding area (119d) in the large support stand printing device (110a) as shown in FIG. 1. In other embodiment, the biodegradable materials such as the volatile macromolecule material, the flow-state Polylactide (PLA) with dissolved-solution added or Polycaprolactone etc. is filled in the material feeding area (119d) in the small support stand printing device (110b) as shown in FIG. 1. In another embodiment, the human-body fiber mother cell is filled in the material feeding area (119d) in the cell printing device (110c) as shown in FIG. 1.

Under this disposition, through the chiller (not shown in the Figure), having the ice water at 4-degree C. from the first temperature modulation pipeline (118g) enter the heat-exchange area (118f) and through second temperature modulation pipeline (118h) to carry the ice water away from the heat-exchange area (118f), it is capable of having the 4-degree ice water perform circulation with the heat-exchange area to make the temperature-controlled modulation module (118) maintain at the state of low temperature. However, it is not limited in the present embodiment, in the other embodiment, the temperature-controlled modulation module is capable of having different fluid pass through according to the temperature control requirements, for instance, ice water under the room temperature, hot water above the room temperature, refrigerant, coal-burning oil, various fluids that is capable of performing heat exchange reaction. In another embodiment, the temperature-controlled modulation module is also capable of performing cooling and heating control through refrigerating chip or electric heating.

Figure 10:
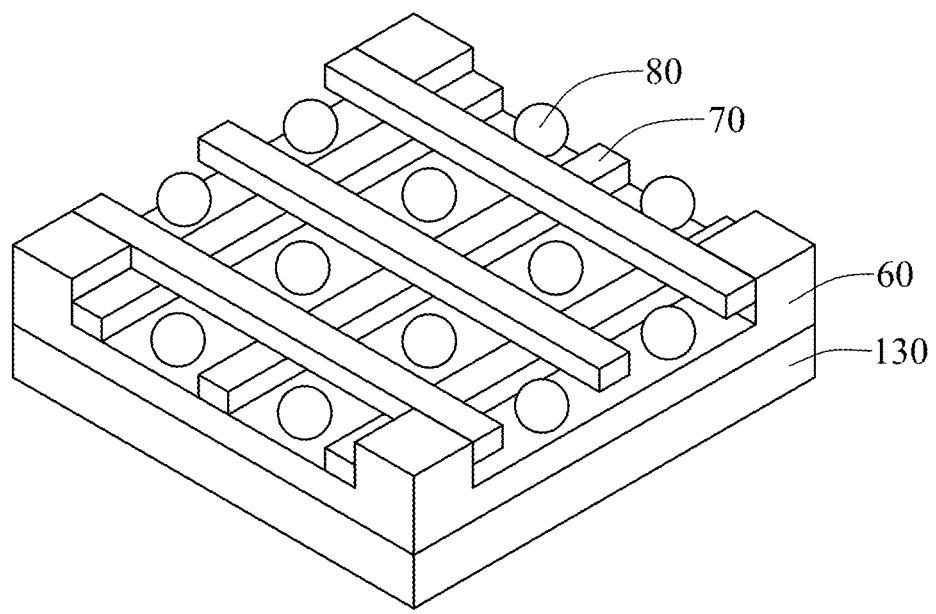
FIG. 10 is a schematic drawing showing the printing performance of the three dimensional tissue of the disclosure.

FIG. 10 is a schematic drawing showing the printing performance of the three dimensional tissue of the disclosure. As shown in FIG. 10, after completing the introduction of the structure of the above-mentioned three dimensional tissue printing device, subsequently, the large support stand printing device (110a), small support stand printing device (110b) and cell printing device (110c) are introduced as follows:

As far as the large support stand printing device (110a) is concerned, it is used for filling a temperature-reaction type material which is mainly a collagen. The characteristics of the collagen are as follows: (a) The collagen is capable of appearing flow-state if it is maintained below 4° C. temperature; (b) The collagen is capable of appearing quasi-plastic-state if it is heated to 37° C. temperature; (c) The collagen is capable of performing reversible reaction if it is maintained between 4° C. and 37° C. temperature. In other embodiment, the temperature-reaction type material can be melt-state material, the biodegradable materials such as a flow-state Polylactide (PLA) with dissolved-solution added, or a polycaprolactone (PCL) etc.

Under this disposition, temperature-controlled modulation module (118) is employed to cool down the temperature-reaction type material, the three dimensional moving platform (120) moves the large support stand printing device (110a) which has the temperature-reaction type material, after being cooled, squeeze out to the carrier unit (130), the heating element (140) has the temperature-reaction type material, after being cooled down, to be heated to form the first printing body (60) as shown in FIG. 10.

To explain in detail, in the process that the large support stand printing device (110a) prints the first printing body (60), the temperature-reaction type material is contained in the material feeding area (119d) (e.g. FIG. 7) of the injection barrel (119b). In the present embodiment, the temperature-reaction type material is collagen for example, and the injection barrel (119b) is penetrated in the temperature-controlled modulation module (118) which, employs the above-mentioned cooling mode and is capable of maintaining a low temperature of below 4° C. temperature, makes the temperature-reaction type material in the injection barrel (119b) appear flow-state while the way of cooling has been mentioned above and is not going to repeat here.

Subsequently, pushing the injection push rod (119a) to make the temperature-reaction type material, after being cooled down, squeeze out from the pinhead (119c) to the carrier unit (130) while, through the cool-guidance washer (118c), make the pinhead (119b) capable of maintaining a low temperature of below 4° C. temperature and enhancing the cool-maintaining effect of the temperature-reaction type material contained in the injection barrel (119b). Besides, by making use of the movement of the three dimensional moving platform (120) to let the pinhead (119c) and carrier unit (130) generate relative movement and, also through the heating action of the heating element (140) for curing the temperature-reaction type material after being cooled to form the first printing body (60), and the first printing body (60), after being cured, is capable of providing a main support stand that possesses strength.

Figure 8:
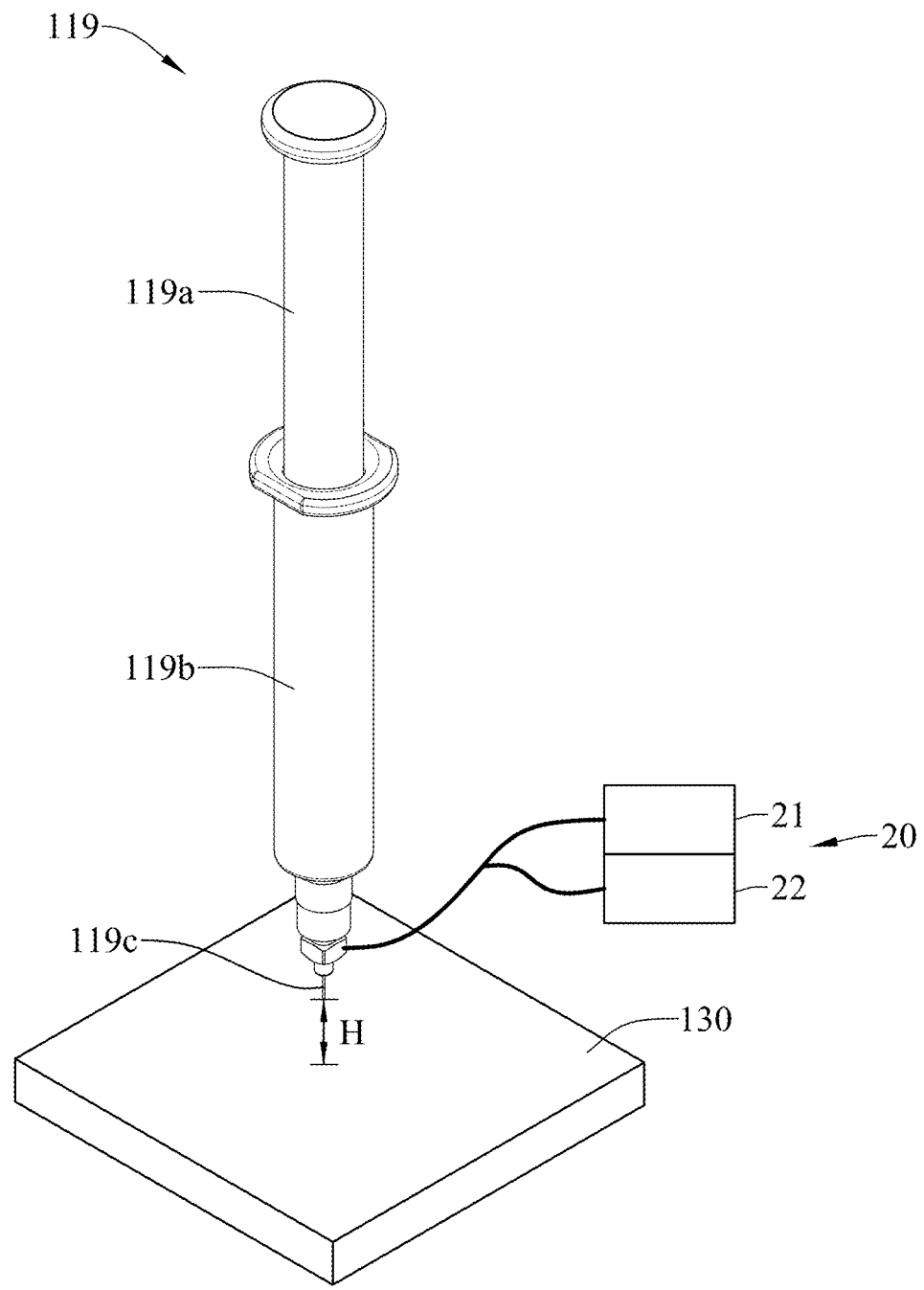
FIG. 8 is a schematic drawing of the injection device of the small support stand printing device of the disclosure.
Figure 9:
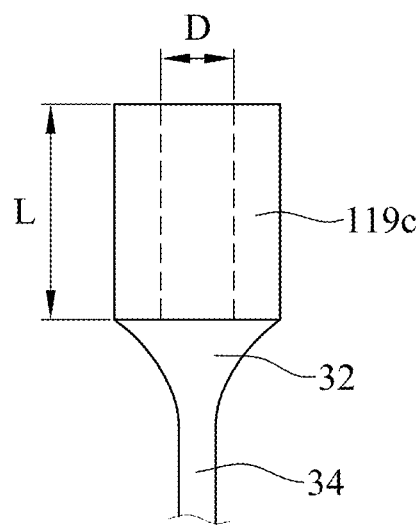
FIG. 9 is a schematic drawing showing when the small support stand printing device is performing printing in FIG. 8 of the disclosure.

FIG. 8 is a schematic drawing of the injection device of the small support stand printing device of the disclosure while FIG. 9 is a schematic drawing showing when the small support stand printing device is performing printing in FIG. 8 of the disclosure. As shown in FIG. 1, FIG. 8, and FIG. 9, as far as the small support stand printing device (110b) is concerned, the three dimensional tissue printing device (100) further includes an electric field auxiliary system (20) which is coupled to the injection device (119) and the carrier unit (130).

The electric field auxiliary system (20) includes a power supply (21) and a voltage controller (22).

The small support stand printing device (110b) is used for filling a material which, for example, is the biodegradable materials such as a volatile macromolecule material, a flow-state Polylactide (PLA) with dissolved-solution added, or a polycaprolactone (PCL), and so forth. In other embodiment, the material can also be the one possessing flow-state by the use of a solid state drawing snag, powders, or granular state, and through the process of stirring, melting, or heat melting.

Under this disposition, having the small support stand printing device (110b) be activated by voltage, a voltage difference is generated between the an injection device (119) of the small support stand printing device (110b) and the carrier unit (130) making the material in the small support stand printing device (110b) form a micro jet stream, while the three dimensional moving platform (120) moves the small support stand printing device (110b) making the micro jet stream print on the first printing body (60) and form a second printing body (70) and making a tissue structure (e.g.

as shown in FIG. 10) crossly-connected form between the first printing body (60) and second printing body (70).

To state in detail, while the small support stand printing device (110b) is printing the second printing body (70), the material is contained in the material feeding area (119d) (as shown in FIG. 7) of the injection barrel (119b), by means of moving the an injection device (119) by the three dimensional moving platform (120), the pinhead (119c) is made to maintain a distance H with the carrier unit (130) where the distance H is between 0.2 mm through 5 mm.

The voltage controller (22) being used for providing a voltage condition is output to the pinhead (119c) through the power supply (21), wherein the voltage condition is the relative voltage difference provided in the range of 10 through 30 kv between the pinhead (119c) and the carrier unit (130). In the present embodiment, the pinhead (119c) is connected to positive voltage, however, the present embodiment is not limited to this, the pinhead (119c) can be either connected to negative voltage or to the ground in other embodiments.

Subsequently, pushing the injection push rod (119a) to make the material flow out from the pinhead (119c). As the surface of the material being subjected to traction generates electric charge polarity and accumulate near the tip of the pinhead (119c). These accumulated electric charges makes the material form a Taylor cone (32) (as shown in FIG. 9) at the tip of the pinhead (119c) and generate a micro jet stream (34) spraying out from the Taylor cone (32). Besides, by making use of the movement of the three dimensional moving platform (120) to let the pinhead (119c) and carrier unit (130) generate relative movement, the micro jet stream (34) is printed on the first printing body (60) forming the second printing body (70) (as shown in FIG. 10) which is capable of providing cell connection.

Comparing with the first printing body (60), since the line width of the second printing body (70) printed by the small support stand printing device (110b) is relatively small, they can be constructed between the previous first printing bodies (60). As shown in FIG. 10, the second printing body (70) includes a multiplicity of long strips that are perpendicular and connected to the ones on the first printing body (60) and are contained thereof for providing sufficient mechanical strength. Moreover, the long strip structures of the second printing body (70) are crossly connected with the ones in the first printing body (60) to form a plurality of cell-disposed spaces for providing the cultivation and proliferation for the cells with stable growth environment.

As far as the cell printing device (110c) is concerned, the cell printing device (110c) is used for filling the human-body fiber mother cells (80) which are contained in the material feeding area (119d) (as shown in FIG. 7) of the injection barrel (119b). Under this disposition, the three dimensional moving platform (120) moves the cell printing device (110c) making the human-body fiber mother cells (80) instill into the tissue structure formed by crossly connecting between the first printing body (60) and the second printing body (70). Moreover, by means of the Z-axis driving element (126) of the three dimensional moving platform (120), the cell printing device (110c) is made to perform reciprocating movement (e.g. make the cell printing device 110c perform up-and-down linear motion in Z-axis direction) making the human-body fiber mother cells (80) perform stirring action to improve the density uniformity of the cell instillation.

Figure 11:
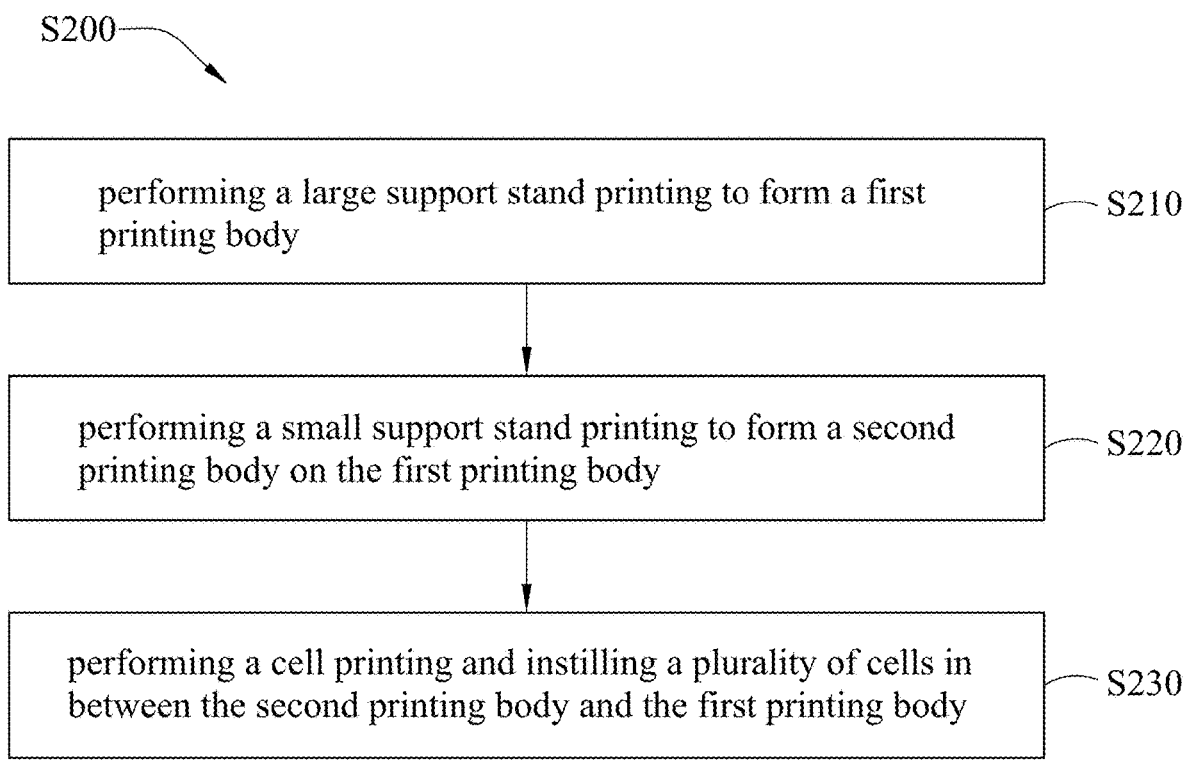
FIG. 11 is the flow chart of the printing method of the three dimensional tissue of the disclosure.

FIG. 11 is the flow chart of the printing method of the three dimensional tissue of the disclosure. As shown in FIG. 11, the three dimensional tissue printing method S200 in the present embodiment includes the following step S210 through step S230:

What is needed to explain that the three dimensional tissue printing method S200 includes a pre-operating flow chart.

Firstly, Providing the three dimensional tissue printing device (100) as shown in FIG. 1.

Subsequently, printing the parameter set-up, for instance, the parameters of the set-up of cooling temperature, printing path, printing speed, voltage strength, the distance between the pinhead (119c) and the carrier unit (130) etc.

Afterward, Feeding the printing material: take the large support stand printing device (110a) for example, as shown in FIG. 7, having the temperature-reaction type material feed into the material feeding area (119d). In this way, the pre-operating flow chart is substantially completed.

Performing Step S210, Performing a large support stand printing to form a first printing body.

Figure 12:
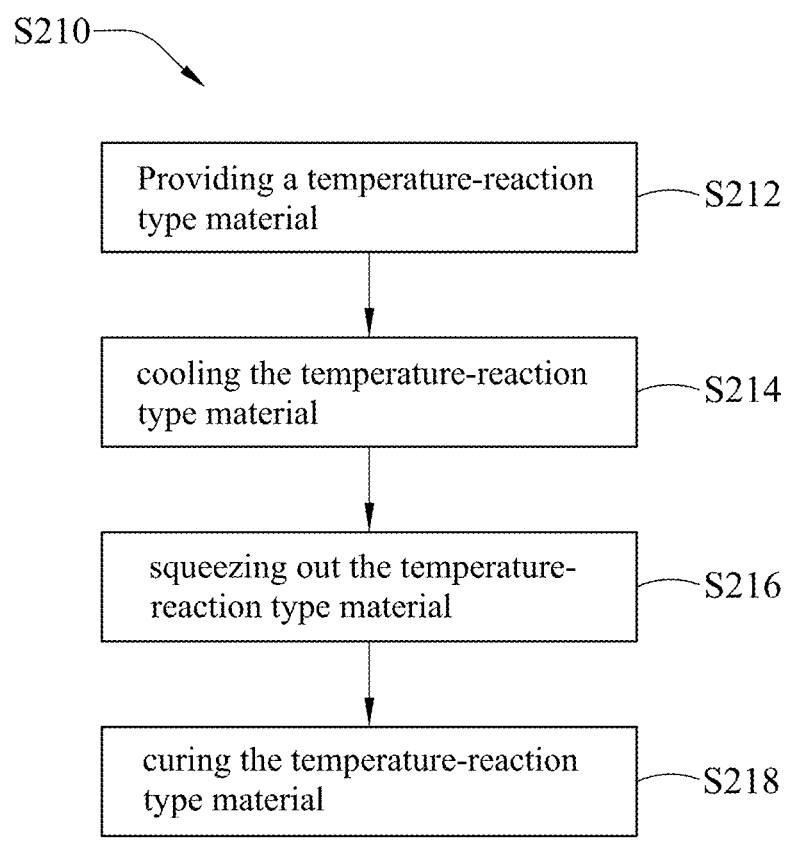
FIG. 12 is the schematic drawing of the further flow chart of the large support stand printing of the disclosure.

The Step S210 further includes the following steps: FIG. 12 is the schematic drawing of the further flow chart of the large support stand printing of the disclosure, as shown is FIG. 12 which is a further schematic flow chart drawing of the large support stand printing of FIG. 11.

Performing Step S212, provides a temperature-reaction type material.

The temperature-reaction type material is a collagen. In other embodiments, the temperature-reaction type material can be biodegradable materials such as a melt-state material, Polylactide (PLA) of added dissolved-solution or polycaprolactone (PCL) etc.

Subsequently, Step S214 is performed, cooling temperature-reaction type material.

The step for cooling the temperature-reaction type material includes making the temperature-reaction type material appear flow-state. As far as the present embodiment is concerned, cooling the temperature-reaction type material till below 4° C. temperature and maintaining below 4° C. temperature makes the temperature-reaction type material appear flow-state.

Subsequently, performing the Step S216 to squeeze out the temperature-reaction type material.

As far as the present embodiment is concerned, the driving motor (112) drives the driving-sliding platform (114) making the ball screw (114b) and the ball screw nut (114i) relatively rotate. Since both ends of the ball screw (114b) are pivotally supported, the ball screw nut (114i) is driven to rotate by the ball screw (114b), and together with the securing member (114a) and the two linear bushings (114j) to perform up-and-down linear motion in Z-direction so as to push the injection push rod (119a) to move along inside the injection barrel (119b) so as to squeeze out the temperature-reaction type material in the injection barrel (119b). In other embodiments not shown in the Figures, a guidance mode of linear sliding rail and slider can be employed or a pneumatic pushing mode can also be employed to push the injection push rod (119a) to be moved within the injection barrel (119B), but the present embodiment is not limited to these.

Besides, in the process of squeezing out the temperature-reaction type material, the three dimensional moving platform (120) is employed to make the pinhead (119c) move, and the moving path can be various modes of shapes such as zigzag, dendritic, mesh structure, concentric circle and helical etc. to form through required printing framework, however, the present embodiment is not limited to these, it all depends on the real requirements to adjust the printing framework.

Subsequently, the Step S218 is performed to cure the temperature-reaction type material.

In the Step S218 of curing the temperature-reaction type material includes heating the temperature-reaction type material to make it appear a quasi-plastic state to form the first printing body for providing the main support stand which possesses strength.

Referring again to FIG. 11 to perform the Step S220, performing a small support stand printing to form a second printing body on the first printing body, wherein a tissue structure is crossly-connected formed between the first printing body and the second printing body.

What is needed to depict is that after completing the Step S210, the process will come back to the pre-operating flow chart. At this moment, in the process of setting up the printing parameter, the set-up of the printing path, printing speed, voltage strength, the distance H between the pinhead (119c) and the carrier unit (130) wherein the distance H is between 0.2 mm through 5 mm.

When it comes to filling the material, taking the small support stand printing device (110b) for example, having the biodegradable materials such as a volatile macromolecule material, a flow-state Polylactide (PLA) with dissolved-solution added, or a polycaprolactone (PCL), and so forth or the one possessing flow-state by the use of a solid state drawing snag, powders, or granular state, and through the process of stirring, melting, or heat melting fill in the material feeding area (119d) (e.g. FIG. 7) of the injection barrel (119b).

Figure 13:
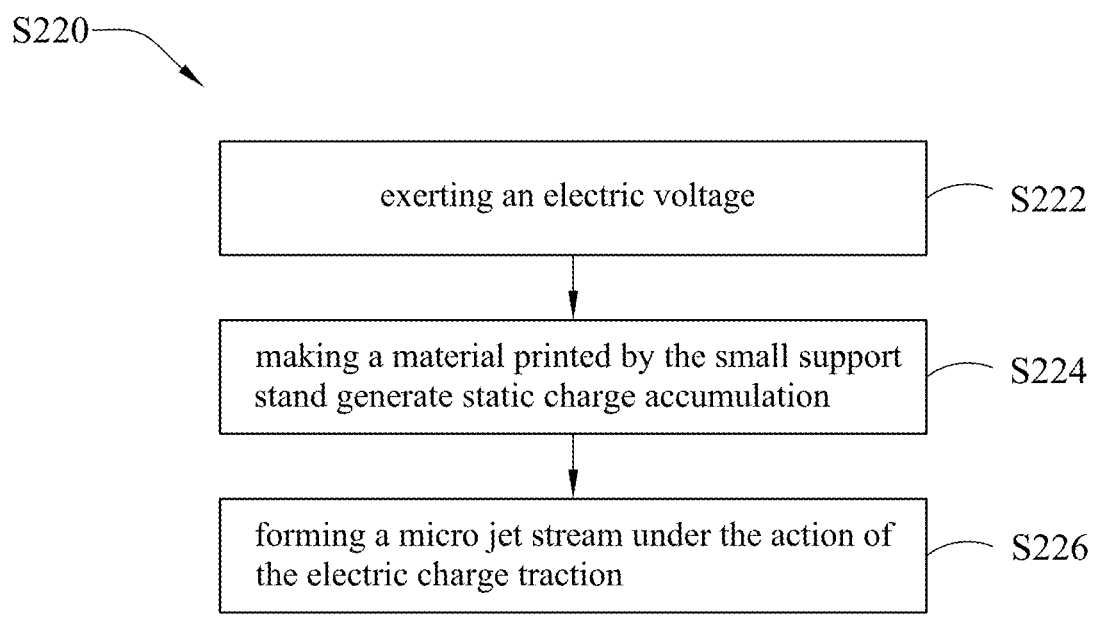
FIG. 13 is the schematic drawing of the further flow chart of the small support stand printing of the disclosure.

FIG. 13 is the schematic drawing of the further flow chart of the small support stand printing of the disclosure. As shown in FIG. 11, the Step S220 further includes the following steps:

First of all, performing the Step S2223, exerting an electric voltage and subsequently, performing Step S224 to make a material printed by the small support stand printing device generate static charge accumulation. Step S226: a micro jet stream is formed under the traction function of the electric charge.

As far as the present embodiment is concerned, by exerting electric voltage, a voltage difference is formed between the small support stand printing device (110b) and carrier unit (130) making the material contained in the small support stand printing device (110b) form a micro jet stream while the three dimensional moving platform (120) moves the small support stand printing device (110b) making the micro jet stream print on the first printing body (60) to form the second printing body (70) as shown in FIG. 10. This second printing body provides cell connection while a tissue structure is formed between the first printing body (60) and the second printing body (70).

What is needed to explain is that after completing the Step S220, it will conducting-through member (140) back to a pre-operating flow chart. At this moment, the following parameter set-up needs to be readjusted: printing path, printing speed, voltage strength, the distance between the pinhead (119c) and the carrier unit (130), and so forth.

Referring again to FIG. 11 to perform Step S230, performing cell printing, infusing a plurality of cell at the tissue framework formed by crossly connecting in between the second printing body and the first printing body.

The steps for performing the cell printing includes: Stirring the plurality of cells which are the human-body fiber mother cells, as shown in FIG. 11, the human-body fiber mother cells (80) are the tissue structure crossly-connected formed between the first printing body (60) and the second printing body (70)

In this way, repeating the step S210 through the step S230 to repeat the printing procedure to be able to form a three dimensional tissue structure.

Referring again to FIG. 10, in the present embodiment, the first printing body (60) is constituted by temperature-reaction type material which being mainly a collagen becomes the first printing body (60) through the process of cooling and curing the temperature-reaction type material.

The second printing body (70) is constituted by materials, e.g. the biodegradable materials such as a volatile macromolecule material, a flow-state Polylactide (PLA) with dissolved-solution added, or a polycaprolactone (PCL) etc. Therefore, the materials form micro jet stream through exerting electric voltage. The micro jet stream is sprayed to print on the first printing body (60) to form a second printing body (70). Besides, a tissue structure is formed by crossly connecting in between the first printing body (60) and the second printing body (70).

The plurality of human-body fiber mother cell (80) is positioned in a tissue structure formed by crossly connecting in between the first printing body (60) and the second printing body (70).

FIG. 14A through FIG. 14D are schematic drawings showing the observation of the printing growth of the cell of the small support stand of the disclosure. As shown in FIG. 14A through FIG. 14D, in an embodiment, this three dimensional tissue structure is capable of applying in the three dimensional skin tissue printing to form an artificial skin. Take the above-mentioned FIG. 10 for example, the first printing body (60) employs collagen, the second printing body (70) employs biodegradable material, while the cell employs human-body fiber mother cell having the cell cultivation liquid employ fetal bovine serum.

Figure 14A:
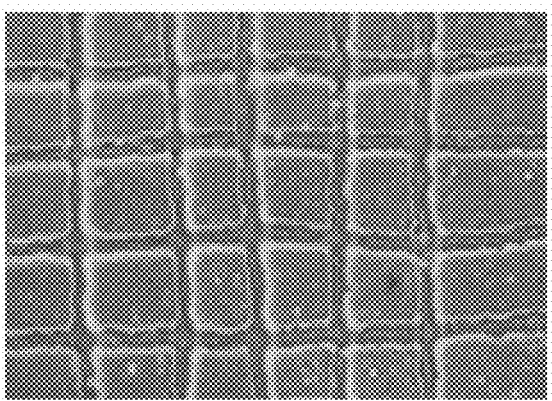
FIG. 14A through FIG. 14D are schematic drawings showing the observation of the printing growth of the cell of the small support stand of the disclosure.
Figure 14B:
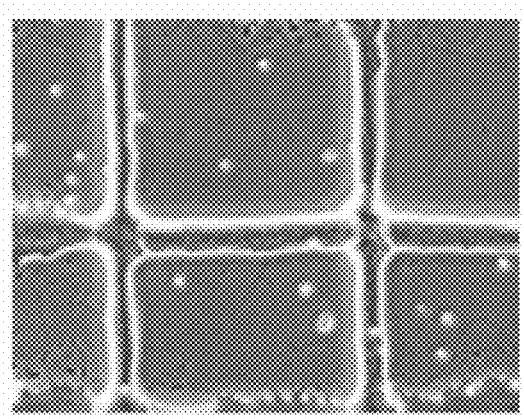
Figure 14C:
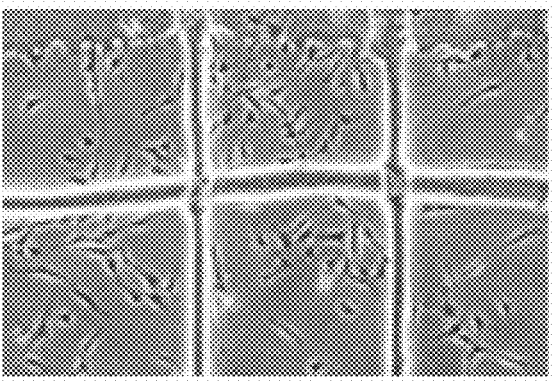
Figure 14D:
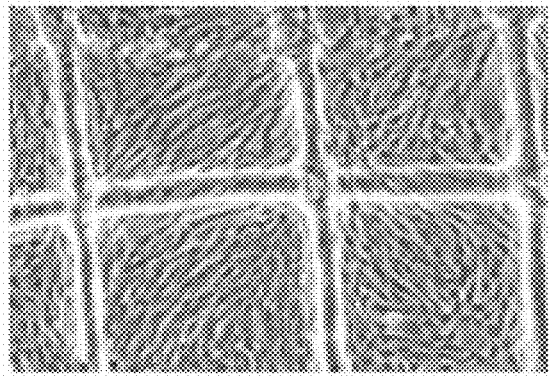
Figure 15:
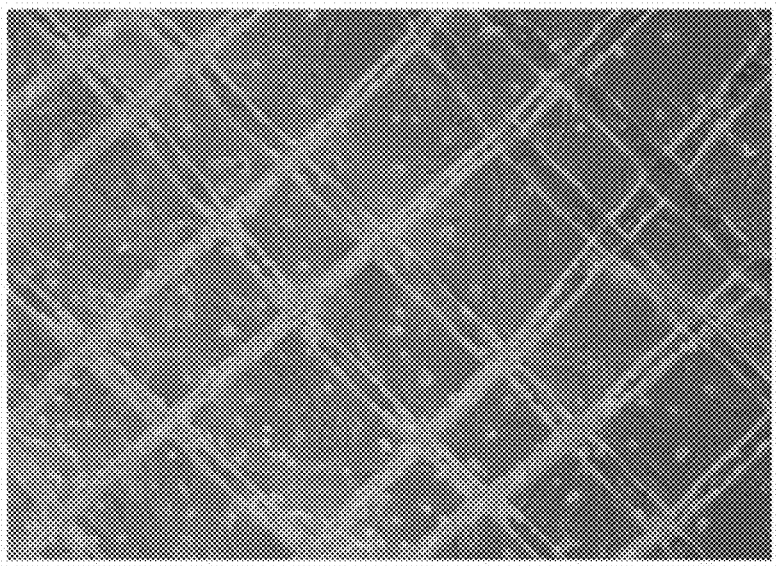
FIG. 15 is a schematic drawing showing the cells positioned at the support stand additive of the disclosure.

Through the substantial printing testing, FIG. 14A represents the printing, by small support stand printing, to become grid with line width being 50~95 μm. FIG. 14B shows that the fiber mother cells, being appear in spherical shapes, are just instilled. As shown in FIG. 14C, the fiber mother cells stickers cover appears slender strips in shape while the fiber mother cells shown in FIG. 14D shows that the fiber mother cells is successfully duplicated and proliferated and connected. As can be seen from FIG. 14B through FIG. 14D, the cells can be maintained printing cell function and also can be successfully proliferated. This is sufficient to prove that the tissue structure made by employing the three dimensional tissue printing device and the three dimensional tissue printing method is capable of providing cell cultivation and the proliferated and stable growth environment. When it comes to applying the three dimensional tissue printing to form artificial skin, since the human-body fiber mother cell that contains growth factors is employed, the human-body fiber mother cell can promote the skin growth without exclusivity. Besides, FIG. 15 is a schematic drawing showing the cells positioned at the support stand additive of the disclosure.

Figure 16:
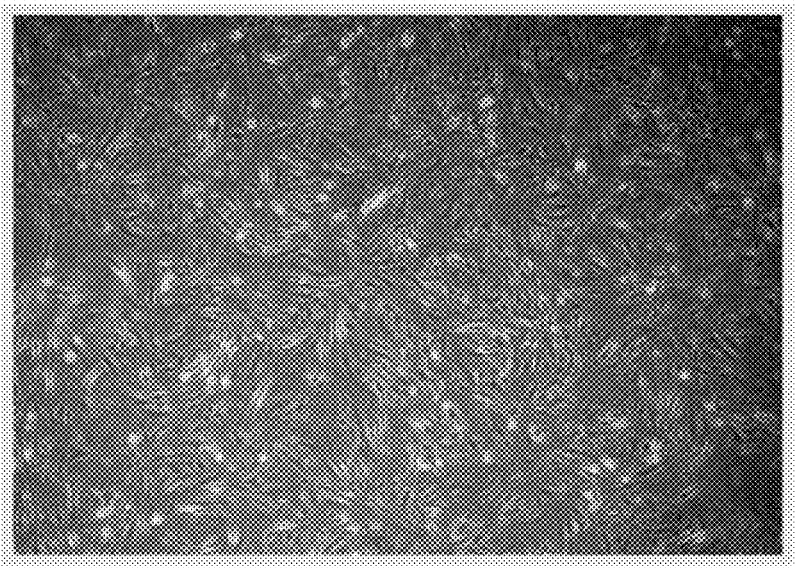
FIG. 16 is the cell tissue crystallographic of the real electric field test of the disclosure.

FIG. 16 is the cell tissue crystallographic of the real electric field test of the disclosure. Please refer to in FIG. 5 and FIG. 16.

As shown in FIG. 9, if the simulated condition will be affected by the pinhead length L, the aperture D of the pinhead, and the surface tension γ of the liquid, the electric voltage of the micro jet stream (34) generated from spraying from the tip of the Taylor cone (32) is called critical voltage $V_c$ and this critical voltage divided by the distance H between the pinhead (119c) and the carrier unit (130) is called critical electric field $E_c$, the calculation formula is as follows:

$$E_c^2 = \frac{2}{L^2}\left(\ln\frac{2}{D} - \frac{3}{2}\right)(0.117\pi\gamma D) \quad (1)$$

Figure 17:
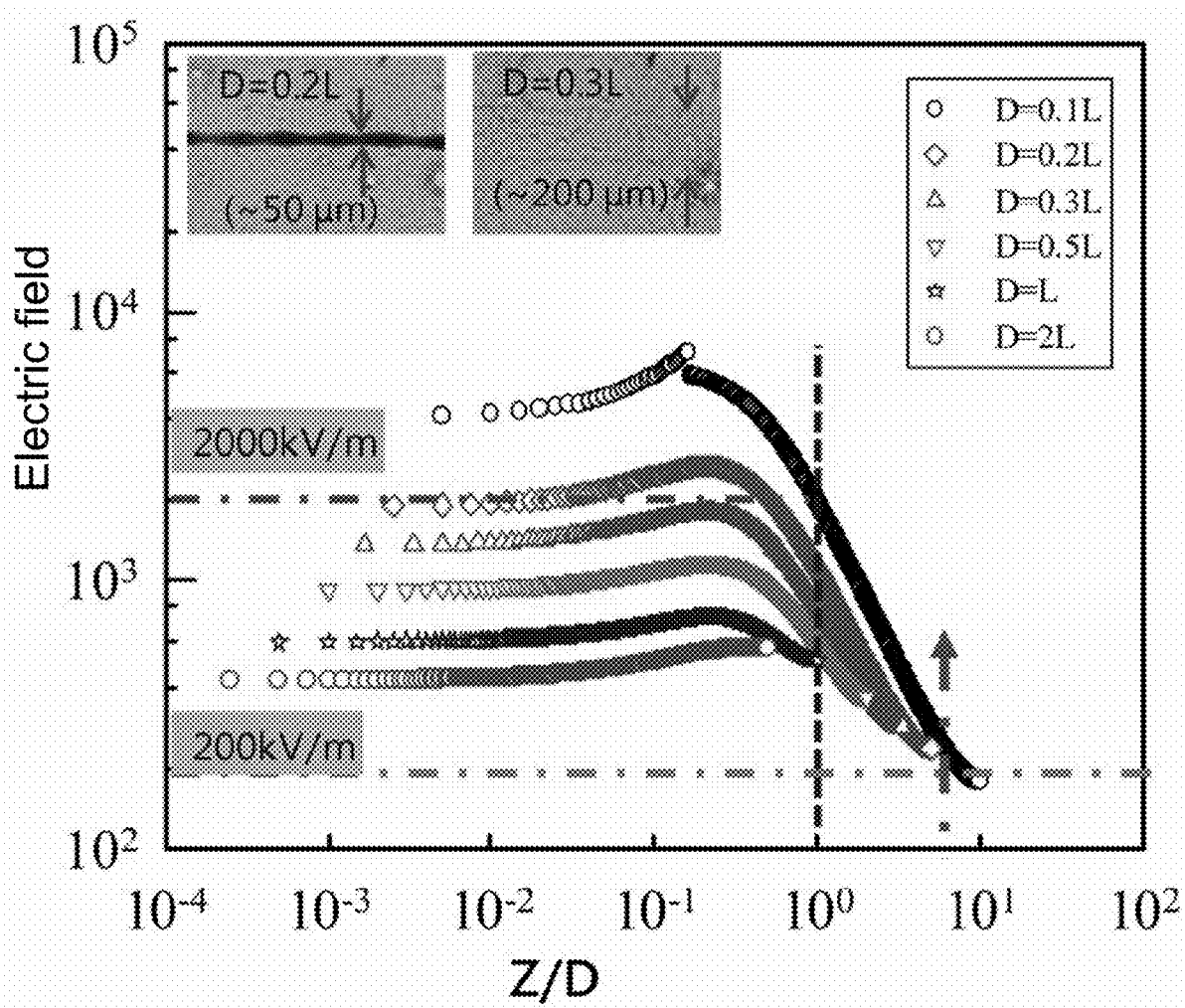
FIG. 17 is a simulated schematic drawing of the small support stand printing device of the disclosure.

FIG. 17 is a simulated schematic drawing of the small support stand printing device of the disclosure. As shown in FIG. 17, it shows the relationship between the ratio of Z/D and the electric field, where Z is the distance between the cultivation dish (50) and the tip of the pinhead (119c), D is the aperture of pinhead. In the present embodiment, if the length of the fixed pinhead is 3 mm, the influence of the pinhead aperture to the jet printing is discussed. The smaller the aperture of the pinhead, through the simulation, the greater the gained electric field and the smaller the sprayed line width of the micro jet stream they are, and the experimental result shows the same trend. Considering the degree of difficulty of manufacturing the pinhead, if the sizes of the pinhead (119c) are that the aperture D=0.6 mm, length of the pinhead L=3 mm, the received area electric field of the carrier unit (130) is around 200 kV/m, then the optimum ratio of Z/D is between 1 through 10 according to the results of the analysis. FIG. 16 is the cell tissue crystallographic of the real electric field test of the disclosure. As shown in FIG. 16, as for the effect of the influence of the high voltage electric field with respect to the cell, the titration of the human-body fiber mother cell is performed, under the pinhead of the small support stand printing device, the cell is substantially scanned by 200 kV/m of electric field for 10 minutes and cultivated for 48 hours, the cell is still capable of performing proliferation through observation without being affected by the high voltage electric field. However, the small support stand printing device needs to be exerted by electric voltage only while it is performing printing, but the cell printing device (110c) does not need to be exerted by electric voltage while it is performing printing.

To summarize the above statements, in the three dimensional tissue printing device, three dimensional tissue printing method and artificial skin of the disclosure, the first printing body is constituted by the temperature-reaction type material which appears flow-state through the cooling process. The flow-state temperature-reaction type material performs movingly printing to become first printing body through heating-to-cure process for providing a main support stand that possesses mechanical strength.

Then, by exerting electric voltage, the material forms micro jet stream which prints on a first printing body to form second printing body that provides cell connection. Since the line width of the second printing body is relatively small, they can be constructed between the first printing bodies and the second printing body includes a multiplicity of long strips that are perpendicular and connected to the ones on the first printing body and are contained thereof for providing sufficient mechanical strength and a plurality of cell-disposed spaces are formed for providing the cultivation and proliferation for the cells with stable growth environment.

Moreover, the human-body fiber mother cell instills in between the first printing body and the second printing body and are crossly connected to form a tissue structure, and the printing process is repeated to form a three dimensional tissue structure so as to provide the integrity and mechanical strength of the three dimensional tissue structure. Besides, the precision of printed microstructure is improved down to 20~200 micrometer structure. It is capable of further maintaining the cell function after printing, establishing a three dimensional tissue structure to avoid the gene mutation and functional variation of the cell.

What is more, when it comes to applying in the three dimensional skin tissue printing and forming artificial skin, as the human-body fiber mother cells employed to make the artificial skin contain growth factors, the artificial skin, formed by the above-mentioned three dimensional tissue printing device and the printing method, can promote the skin growth without exclusivity by the growth factors. Besides, as the three dimensional tissue printing device of the disclosure can set the moving path of the three dimensional moving platform to form the required printing framework according to the requirements (e.g. the range of wound part) of the user, thereby, can accomplish the customer-made printing skin tissue so as to completely stick on the wound part and reduce the risk of wound infection.

It will become apparent to those people skilled in the art that various modifications and variations can be made to the structure of the disclosure without departing from the scope or spirit of the disclosure. In view of the foregoing description, it is intended that all the modifications and variation fall within the scope of the following appended claims and their equivalents.

What is claimed is:

1. A three dimensional tissue printing device, comprising:
   a three dimensional moving platform;
   an instillation unit connected to the three dimensional moving platform, wherein the instillation unit comprises:
      a large support stand printing device configured to fill a temperature-reaction type material further comprising a temperature-controlled modulation module;
      a small support stand printing device configured to fill a material;
      a driving-sliding platform;
      a driving motor, connected to the driving-sliding platform, wherein the temperature-controlled modulation module is furnished at the driving-sliding platform; and
      an injection device, further comprising:
         an injection barrel furnished into the temperature-controlled modulation module;
         a pinhead, furnished at an end of the injection barrel; and
         an injection push rod, with an end thereof pivotally furnished at the injection barrel and the other end thereof connected to the driving-sliding platform;
   a carrier unit connected to the three dimensional moving platform and positioned opposite to the instillation unit, the carrier unit having a heating element; and
   an electric field auxiliary system which is coupled to the injection device and the carrier unit, the electric field auxiliary system further comprising a power supply and a voltage controller, wherein the small support stand printing device is configured to print a second printing body and the injection barrel is configured to contain the material, and the three dimensional moving platform is configured to move the injection device, such that a distance exists between the pinhead and the carrier unit; the voltage controller is configured to provide a voltage condition output to the pinhead through the power supply, and the movement of the three dimensional moving platform is configured to generate relative movement by the pinhead and the carrier unit.

2. The three dimensional tissue printing device as claimed in claim 1, wherein the instillation unit further comprises a cell printing device configured to fill a human-body fiber mother cell, and the three dimensional moving platform is configured to move the cell printing device.

3. The three dimensional tissue printing device as claimed in claim 2, wherein by means of a Z-axis driving element of the three dimensional moving platform, the cell printing device is configured to perform reciprocating movement.

4. The three dimensional tissue printing device as claimed in claim 1, wherein the large support stand printing device contains the temperature-reaction type material, wherein the temperature-reaction type material is a collagen, a melt-state material, a flow-state Polylactide (PLA) with dissolved-solution added, or a polycaprolactone (PCL).

5. The three dimensional tissue printing device as claimed in claim 1, wherein the small support stand printing device contains the material, wherein the material is a volatile macromolecule material, the flow-state polylactide (PLA) with dissolved-solution added or polycaprolactone (PCL).

6. The three dimensional tissue printing device as claimed in claim 1, wherein the small support stand printing device contains the material, wherein the material is a solid state drawing snag, powders, or granular state, and through a process of stirring, melting, or heat melting, becomes flow-state material.

7. The three dimensional tissue printing device as claimed in claim 1, wherein the injection device further comprises a syringe platen, wherein the injection barrel is furnished into the temperature-controlled modulation module and the syringe platen is furnished into the temperature-controlled modulation module for holding the injection barrel.

8. The three dimensional tissue printing device as claimed in claim 1, wherein the large support stand printing device is configured to print the first printing body and the injection barrel penetrated in the temperature-controlled modulation module is configured to contain the temperature-reaction type material, and the temperature-controlled modulation module is configured to make the temperature-reaction type material appear flow-state, and the injection push rod is configured to push the temperature-reaction type material that has been cooled down out from the pinhead to the carrier unit, and the three dimensional moving platform is configured to move to generate relative movement with respect to the carrier unit, and the temperature-reaction type material cured through the heating of the heating element and cooled down is configured to form the first printing body.

9. The three dimensional tissue printing device as claimed in claim 1, wherein the distance between the pinhead and the carrier unit is in the range of 0.2 mm through 5 mm.

10. The three dimensional tissue printing device as claimed in claim 1, wherein the voltage condition is the relative voltage difference provided between the pinhead and the carrier unit is in the range of 10 through 30 kv.

11. The three dimensional tissue printing device as claimed in claim 1, wherein the temperature-controlled modulation module further comprises:
a cooling water ring jacket;
a cooling inner ring, having the injection barrel position therein, is furnished in the cooling water ring jacket a heat-exchange area formed between the cooling water ring jacket and cooling inner ring;
a cool-guidance washer positioned between the front end of the injection barrel and the cooling water ring jacket; and
an O-ring position positioned between cooling water ring jacket and the cooling inner ring.

12. The three dimensional tissue printing device as claimed in claim 1, wherein the instillation unit further comprises a rapidly releasing platen assembly furnished on the driving-sliding platform, and the injection push rod is connected to the driving-sliding platform by the use of the rapidly releasing platen assembly.

13. The three dimensional tissue printing device as claimed in claim 12, wherein the driving-sliding platform further comprises:
a ball screw, penetrated through the ball screw nut;
two guided rods, positioned on both sides of the ball screw and are correspondingly penetrated through the two linear bushings;
a securing member;
a ball screw nut, positioned at the securing member; and
two linear bushings, positioned at the securing member and both sides of the ball screw nut;
wherein, as both ends of the ball screw are pivotally supported, and the securing member is capable of performing up-and-down linear movement in Z-direction on the two guided rods.

14. The three dimensional tissue printing device as claimed in claim 13, wherein the driving-sliding platform further comprises a connecting member, an indentation, and two first magnetic elements, the connecting member is connected to the securing member, the indentation is formed at the connecting member, and the two first magnetic elements are positioned in the indentation, the rapidly releasing platen assembly includes a platen, two embossment added nuts, a push rod screw, a trench, and two second magnetic elements, the two embossment added nuts are furnished on both sides of the platen respectively, the push rod screw is furnished by the two embossment added nuts and the platen configured to be penetrated through, and an end of the push rod screw is connected to the injection push rod, the trench is formed on the platen, the two magnetic elements are furnished on the platen, and the two second magnetic elements are positioned on both sides of the trench, the first magnetic element and the second magnetic element are mutually attracted and configured to combine the platen to the connecting member.

15. The three dimensional tissue printing device as claimed in claim 1, wherein the three dimensional moving platform further comprises a base seat, an X-axis driving element, a Y-axis driving element, and a Z-axis driving element which are furnished on the base seat respectively, and the instillation unit is furnished in the Z-axis driving element.

* * * * *